(12) United States Patent
Schell

(10) Patent No.: US 6,250,133 B1
(45) Date of Patent: *Jun. 26, 2001

(54) METHOD FOR DETECTING VENTING OF A COMBUSTION APPLIANCE WITHIN AN IMPROPER SPACE

(75) Inventor: Michael B. Schell, Santa Barbara, CA (US)

(73) Assignee: Edwards Systems Technology, Inc., Cheshire, CT (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/004,142

(22) Filed: Jan. 6, 1998

(51) Int. Cl.[7] .......................... G01N 33/497; G08B 17/10
(52) U.S. Cl. ............................ 73/23.31; 340/632
(58) Field of Search .................. 73/23.2, 23.31; 250/343; 340/632; 126/116 A

(56) References Cited

U.S. PATENT DOCUMENTS

| | | | |
|---|---|---|---|
| 3,826,920 | 7/1974 | Woodroffe et al. | 250/373 |
| 3,922,656 | 11/1975 | Horvath et al. | 340/237 |
| 4,688,021 | 8/1987 | Buck et al. | 340/521 |
| 4,742,761 * | 5/1988 | Horstman | 454/74 |
| 4,763,115 | 8/1988 | Cota | 340/628 |
| 5,026,992 * | 6/1991 | Wong | 250/343 |
| 5,053,754 * | 10/1991 | Wong | 340/632 |
| 5,060,508 | 10/1991 | Wong | 73/31.02 |
| 5,079,422 * | 1/1992 | Wong | 250/343 |
| 5,103,096 * | 4/1992 | Wong | 250/343 |
| 5,159,315 | 10/1992 | Schultz et al. | 250/539 |
| 5,163,332 | 11/1992 | Wong | 73/863.23 |
| 5,204,265 | 4/1993 | Nelson et al. | 436/8 |
| 5,215,498 | 6/1993 | Wong et al. | 454/208 |
| 5,333,487 | 8/1994 | Kimura et al. | 73/23.31 |
| 5,341,214 | 8/1994 | Wong | 356/437 |
| 5,369,397 * | 11/1994 | Wong | 340/632 |
| 5,376,924 | 12/1994 | Kubo et al. | 340/632 |
| 5,445,160 | 8/1995 | Culver et al | 128/719 |
| 5,480,611 | 1/1996 | Mills et al. | 422/56 |
| 5,550,752 | 8/1996 | Federspiel | 364/505 |
| 5,592,147 | 1/1997 | Wong | 340/522 |
| 5,623,105 | 4/1997 | Liston et al. | 73/863.81 |
| 5,625,139 | 4/1997 | Stormbom | 73/23.21 |
| 5,650,054 | 7/1997 | Shen et al. | 204/412 |
| 5,682,145 | 10/1997 | Sweetman et al. | 340/632 |
| 5,691,704 | 11/1997 | Wong | 340/628 |
| 5,694,118 | 12/1997 | Park et al. | 340/632 |

* cited by examiner

Primary Examiner—Hezron Williams
Assistant Examiner—Jay L. Politzer
(74) Attorney, Agent, or Firm—Pepper Hamilton LLP

(57) ABSTRACT

A method for detecting improper venting of a combustion appliance within an interior space relies upon a carbon dioxide detector to determine whether a preselected criterion indicative of improper venting is exceeded. The preselected criterion can be a threshold concentration of carbon dioxide or a threshold level of rate of rise of carbon dioxide concentration that is exceeded at a specified time or over a specified interval of time. The method can be used to detect leaks in a residential furnace, at very low levels, during start up of the furnace by measuring the preselected criterion in a heated air duct.

19 Claims, 2 Drawing Sheets

METHOD FOR DETECTING VENTING OF A COMBUSTION APPLIANCE WITHIN AN IMPROPER SPACE

FIELD OF THE INVENTION

The present invention is in the field of detecting leaks in combustion appliances.

BACKGROUND OF THE INVENTION

The presence of combustion fumes in housing is a significant and serious problem that can cause chronic illness and accidental death. It has been estimated that approximately 500 accidental deaths per year in the U.S. are attributable to improper venting of combustion fumes in housing. Combustion fumes can result from fuel fired appliances like furnaces, water heaters, gas ranges, gas dryers, portable heaters, wood stoves and fireplaces. Research on combustion spillage from combustion appliances has estimated that 30 to 80% of homes in heating climates have incidence of combustion fumes venting into the occupied spaces of houses. Combustion fumes can contain a variety of toxic and harmful gases including nitrous oxide, nitrogen dioxide, sulfur dioxide, carbon monoxide, hydrocarbons and respirable particulates. Carbon dioxide, oxygen and nitrogen are also the non-toxic and major constituent byproducts of the combustion exhaust.

Causes of combustion exhaust entrainment in homes include: malfunctioning equipment, cracked or broken flues and heat exchangers, improper installation, lack of maintenance, tight building construction and the creation of negative pressures in the home that can cause reversal of combustion fumes in chimneys and flues.

In response to this serious problem, there has been rapid growth in the sale of carbon monoxide alarms for home use. In 1997 there were approximately 5 million residential carbon monoxide detectors sold in the U.S.

There are a number of drawbacks to the use of current CO sensors in homes.

The first of these drawbacks is that since these products are only targeted to measure carbon monoxide they are only addressing one of many harmful byproducts of combustion. In fact, some byproducts like nitric oxide have the same physiological effect as carbon monoxide but at one third to one fifth the concentration level. Very low concentrations of other byproducts like nitrogen dioxide have been shown in numerous studies to increase the incidence of respiratory symptoms and illness in children. Carbon monoxide sensors do not provide complete protection from exposure to combustion fumes.

Another drawback of the currently used CO sensors is that residential carbon monoxide sensors have been very problematic in operation. There have been widespread reports of false alarms, susceptibility to alarm when exposed to common household chemicals and malfunctioning alarms. A recent evaluation of four major brands of commercially available residential CO sensors by the Gas Research Institute found that for some brands up to one out of three units will fail to alarm at UL specified concentrations.

Finally, most of the detectors available on the market today are not accurate for measuring concentrations below 60 ppm of carbon monoxide, which may be harmful to adults over prolonged exposure and may cause chronic health problems for children, the elderly and individuals with heart and respiratory problems.

Accordingly, there exists a compelling need for better methods of detecting improper venting of combustion appliances, especially within interior spaces such as homes. In addition, there is also a need for early detection of low levels of improper venting. By identifying low levels of leakage before they become larger, remedial steps can be taken before leakage becomes larger and potentially more dangerous, if not deadly.

SUMMARY OF THE INVENTION

The present invention is generally directed to a method for detecting venting of a combustion appliance within an improper space by using a carbon dioxide detector to determine whether a preselected criterion indicative of venting within the improper space is exceeded and generating an alarm signal if the preselected criterion is exceeded.

In a first, separate aspect of the present invention, the preselected criterion can be varied between several criteria, or more than one of the criteria can be used at once and an alarm signal can be generated when any of the criteria are exceeded. One preselected criterion can be a threshold concentration of carbon dioxide. Another preselected criterion can be a threshold level of rate of rise of carbon dioxide concentration. Still another preselected criterion can be a threshold level of rate of rise of carbon dioxide concentration which is exceeded over a preselected number of consecutive operational cycles of the combustion appliance.

In another, separate aspect of the present invention, the preselected criterion is measured in a heated air duct that is connected to the combustion appliance. The preselected criterion can be measured during start up of the combustion appliance to determine a warm up value of the preselected criterion before a fan begins blowing heated air through the heated air duct. This allows detection of very low levels of leakage. The preselected criterion can also be measured when the combustion appliance is turned on and the fan has been blowing heated air through the heated air duct for greater than a preselected interval to determine an operational value of the preselected criterion. This allows detection of higher levels of leakage that can be potentially dangerous.

Accordingly, it is a primary object of the present invention to provide a method for detecting improper venting of a combustion appliance.

This and further objects and advantages will be apparent to those skilled in the art in connection with the drawing and the detailed description of the preferred embodiment set forth below.

DETAILED DESCRIPTION OF THE PREFERRED EMBODIMENT

Figure 1:
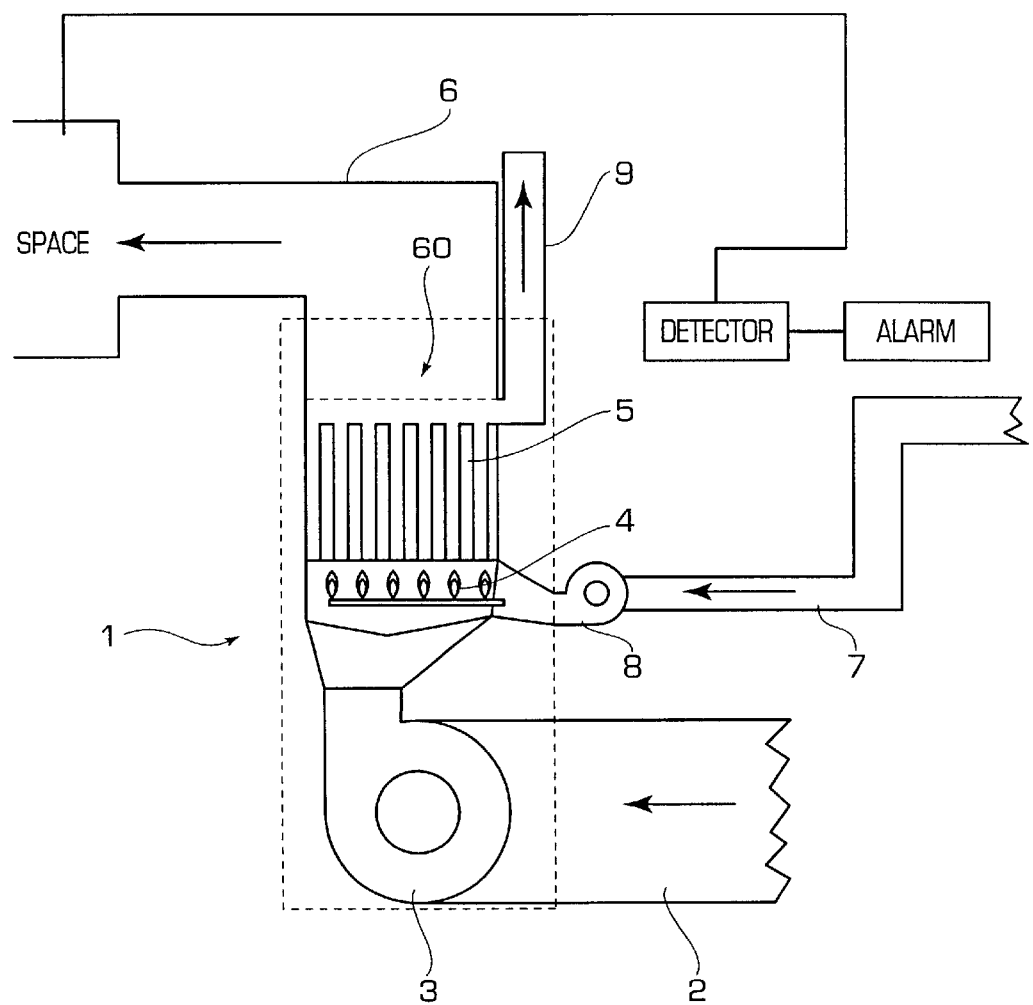
FIG. 1 is a schematic diagram of a preferred embodiment of the present invention in which a carbon dioxide sensor is located in a space downstream from a conventional furnace.

In residential furnace combustion systems, carbon dioxide ($CO_2$) is a major constituent of exhaust gases and is typically present in concentrations of 8 to 15% by volume and nitrogen levels are similar to ambient air at 70–72%. The other more harmful byproducts of the combustion process are present in much lower concentrations ranging from 1 to 400 ppm concentrations in a properly functioning furnace. Concentrations may be ten times higher in an improperly operating furnace.

Because carbon dioxide is present in such high proportions to the other combustion byproducts, certain characteristics of carbon dioxide in a space can be indicative of the presence of combustion byproducts. These characteristics can include an achievement of an absolute threshold level, consistent rate of rise over a predetermined period, or a consistent observed increase of $CO_2$ levels occurring in conjunction with the operation of a particular piece of equipment or in the vicinity of a particular piece of equipment.

Carbon dioxide is present in outside air but at very low concentrations (350 to 450 ppm). Inside buildings people are the major contributors of carbon dioxide and can contribute enough $CO_2$ to allow levels to rise as high as 3000 ppm if a space is poorly ventilated. Levels can go higher, but such elevated concentrations are rare. Accordingly, in a well ventilated building, a $CO_2$ threshold concentration level of 3,000 ppm can be used as a preselected criterion indicative of improper venting of a combustion appliance within the interior space of the building. Alternatively, a $CO_2$ threshold concentration level of 4,000 can be used for general applications to take into account the possibility of poor ventilation. In still another alternative, the threshold could be varied, or reset, based upon operational experience.

As an alternative to measuring a $CO_2$ threshold concentration level as a criterion indicative of improper venting, or in combination with such a measurement, a rate of rise in $CO_2$ concentration can be used as a criterion indicative of improper venting. For most common occupancies in residential structures, modeling studies show that people will contribute $CO_2$ levels that will result in increased $CO_2$ levels of less than 5 ppm per minute. In contrast, similar modeling studies show that a furnace flue if vented directly into a structure can contribute to a rate of rise of 20 to 100 ppm or more per minute. Thus, depending on the location measured and the volume of enclosed space, certain rates of rise in carbon dioxide concentration can be indicative of the presence of combustion fumes. Depending on the volume of the space, certain rates of rise of carbon dioxide concentration will also be indicative of a major combustion leak. For example, a consistent rate of rise of carbon dioxide of over 30 to 50 ppm/minute would be indicative of a furnace or fireplace combustion products leaking into the living space of a house. This type of measurement can be made in the general living space of the house, in the furnace room, in a utility room or in a garage attached to the house. In an especially preferred embodiment of the present invention, a carbon dioxide threshold level or rate of rise of approximately 25 ppm/minute is used as a criterion indicative of improper venting. Also, logic could be built into the device to look for a continuous rate of rise for 5 minutes or more and/or multiple five minute intervals before sounding an alarm signal or warning.

The rate of rise of carbon dioxide can also be measured in the recirculated air plenum of a furnace and/or in the immediate area surrounding the furnace at the time that the furnace is warming up but the air circulation fan has not yet started distributing air through the plenum. (During this period, the heat exchanger is being warmed up). This period typically lasts one to three minutes. A rate of rise in the plenum over this period would be indicative of a heat exchanger leak into the plenum. Further, it should be possible to detect very low levels of leakage during this time period. An alarm could be sounded if a rate of rise greater than approximately zero ppm/minute is detected during the warm up period. Of course, logic could also be used so as not to trigger an alarm upon a single occurrence of detection of a rate of rise during a warm up period, but only once a rate of rise is detected over a consecutive series of warm up periods. By not triggering an alarm signal until a rate of rise is detected over two or more warm up periods, or even over a larger number of warm up periods such as five or more, the possibility of false alarms could be minimized. Also, the threshold level for generating an alarm signal during the warm up period might be raised, or different alarm signals might be generated for different levels of rate of rise. Thus, an initial alarm signal might be generated if a rate of rise greater than approximately zero ppm/minute is detected, a second alarm might be generated if a rate of rise greater than approximately 10 ppm/minute is detected and/or a third alarm might be generated if a rate of rise greater than approximately 25 ppm/minute is detected. Multiple alarm signals could be valuable in interpreting why the alarm signal was generated. For example, if nobody was anywhere near the combustion appliance, a very low alarm signal could be indicative of low leakage. However, such an alarm signal might appropriately be discounted if one or more persons was working near the furnace during the warm up period, or if a very large number of people was present in the dwelling that might generate such a low level rate of rise.

FIG. 1 is a schematic drawing that generically depicts a conventional furnace 1. The furnace 1 has a return air duct 2, an air distribution blower 3, a combustion chamber 4, a heat exchanger 5, a combustion intake 7, a combustion air blower 8 and a flue 9. The furnace 1 is connected to a duct 6.

Figure 2:
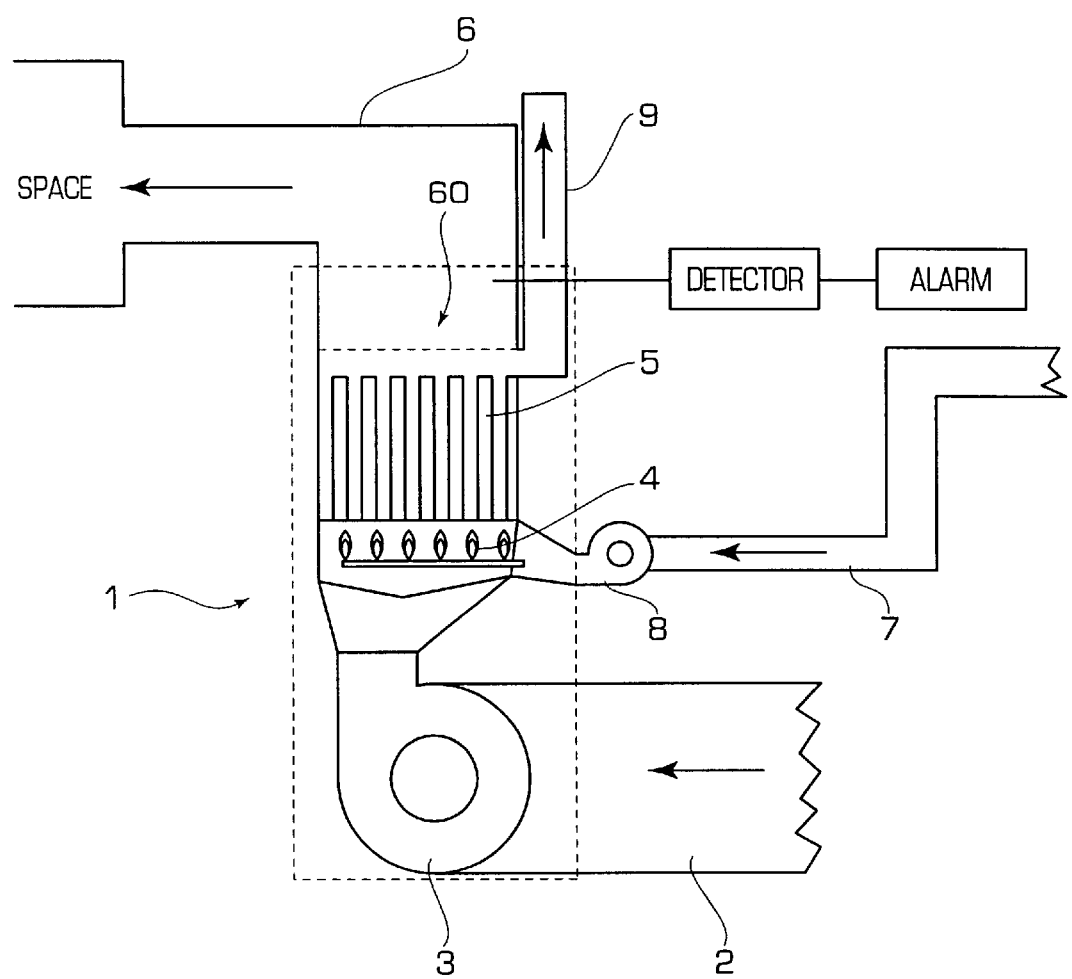
FIG. 2 is a schematic diagram of another embodiment of the present invention in which a carbon dioxide sensor is located in a heated air duct above a conventional furnace.

When furnace 1 is in operation, air is drawn into the combustion chamber 4 through combustion intake 7 where it is combusted, then passed through heat exchanger 5 and then discharged through flue 9. (Although furnace 1 is shown with a combustion air blower 8, such a blower is optional. Some furnaces do not have such a blower when air is drawn directly from ambient air into the combustion chamber due to the natural convective effect of heat rising through the heat exchanger 5 and the flue 9. Such a furnace is often called a naturally aspirating furnace.) The combusted air passed into heat exchanger 5 is used to heat return air that is drawn through return air duct 2 into the air distribution blower 3, passed through heat exchanger 5, and then blown out through an area generally depicted as 60. The heated air duct 60 includes duct 6 and can include some space traditionally considered a portion of the furnace 1. The heated air duct is defined as the portion of the air path on the positive side of the air distribution system downstream from the air distribution blower 3 and the heat exchanger 5. When the preselected criterion is measured in the heated air duct 60, it is especially preferred that the measurement be made as close as practical to the heat exchanger 5 when there is concern about leakage from the heat exchanger 5 (see FIG. 2).

After a furnace is warmed up, it should still be possible to detect improper venting when the air distribution blower 3 is in operation. As the air distribution blower 3 forces air through the heated air duct 60, the heated air should eventually approach an equilibrium condition in which no rate of rise of carbon dioxide concentration is detected. By selecting an interval of time between the time of warm up and the time the rate of rise is measured in the heated air duct 60 during operation of the furnace 1 and the air distribution blower 3 that is sufficient to allow the heated air to approach an equilibrium condition, it is possible to detect improper leakage when the rate of rise subsequently is greater than a nominal rate of rise, such as approximately 5 ppm/minute.

When coupled with a furnace or other appliance, the rate of rise of carbon dioxide can be correlated to the operation of a specific piece of equipment and therefore can be used to isolate or identify the piece of equipment that is causing the carbon dioxide rise and potential venting of combustion fumes into the house or building. Methods of sensing if an appliance or other combustion source is activated could include temperature measurements (identifying significant temperature rises), interlinking with control electronics to sense a current, or activation of a relay when combustion equipment becomes operational. This approach could also be used with a fireplace to identify if it was a source of high carbon dioxide in the space.

In measuring the rate of rise of carbon dioxide concentration, it is not necessary to measure absolute concentrations. The critical point is the relative change in concentrations. In order to minimize costs, it is contemplated that a Non-Dispersive Infrared (NDIR) sensor be used as the carbon dioxide sensor when practicing the method of the preferred embodiment. Accordingly, it would also be possible to use a carbon dioxide detector which relies upon a ratioing technique to determine when a rate of rise in carbon dioxide exceeds what would be equivalent to a given threshold level. A description of a ratioing technique used in an NDIR sensor is set forth in U.S. Patent No. 5,026,992, the disclosure of which is specifically incorporated herein by reference.

It will be readily apparent to those skilled in the art that still further changes and modification in the actual concepts described herein can readily be made without departing from the spirit and scope of the invention as defined in the following claims. For example, it should be possible to design a single apparatus that could be used to practice this invention that includes various logic options and/or is programmable to reset or revise such logic options. Also, the alarm signal can take on any of a variety of forms, such as an audible or visible warning, or it could be an electrical signal sent to a device which acts upon receipt of the alarm signal. Thus, for example, generation of the alarm signal could trigger another event, such as shutting down the combustion appliance, or altering its operation. Alternatively, another device could be triggered into operation to remove or dilute the affect of the improper venting of the combustion device. Accordingly, the scope of this invention is not intended to be limited except as required by the lawful scope of the following claims.

What is claimed is:

1. A method for detecting venting of a combustion appliance within an improper space, comprising the steps of:
   providing a combustion appliance;
   operating the appliance in a manner to generate products of combustion, including carbon dioxide, and to generate heated air;
   providing a space into which venting of the products of combustion is improper;
   directing the products of combustion to a flue away from the improper space;
   directing the heated air from said combustion appliance to a duct connecting to said improper space;
   providing a carbon dioxide detector within the improper space;
   establishing a preselected criterion for carbon dioxide within the improper space that is indicative of venting of products of combustion into the improper space;
   operating the carbon dioxide detector in a manner to determine whether said preselected criterion for venting within the improper space is exceeded; and
   generating an alarm signal in response to detecting that said preselected criterion for venting within the improper space is exceeded.

2. A method as recited in claim 1, wherein the preselected criterion is a threshold concentration of carbon dioxide.

3. A method as recited in claim 2, wherein the threshold concentration of carbon dioxide is approximately 4,000 ppm.

4. A method as recited in claim 1, wherein the preselected criterion is a threshold level of rate of rise of carbon dioxide concentration.

5. A method as recited in claim 4, wherein the threshold level of rate of rise of carbon dioxide concentration is approximately 25 ppm/minute while the combustion appliance is in operation.

6. A method as recited in claim 1, wherein the preselected criterion is a threshold level of rate of rise of carbon dioxide concentration which is exceeded over a preselected number of consecutive operational cycles of the combustion appliance.

7. A method as recited in claim 6, wherein the reduced threshold level of rate of rise of carbon dioxide concentration is approximately 25 ppm/minute while the combustion appliance is in operation.

8. A method as recited in claim 7, wherein the preselected number of consecutive operational cycles is 2 or more.

9. A method as recited in claim 1, wherein the duct includes a heated air duct that is connected to the combustion appliance by a fan.

10. A method as recited in claim 9, wherein the preselected criterion is measured in the heated air duct as close as practical to the heat exchanger.

11. A method as recited in claim 10, wherein the preselected criterion is measured when the combustion appliance is turned on to determine a warm up value of the preselected criterion before the fan begins blowing heated air through the heated air duct.

12. A method as recited in claim 11, wherein the preselected criterion is a rate of rise of carbon dioxide concentration.

13. A method as recited in claim 12, wherein the alarm signal is generated if the warm up value of the preselected criterion is greater than approximately zero ppm/minute.

14. A method as recited in claim 10, wherein the preselected criterion is measured when the combustion appliance is turned on and the fan has been blowing heated air through the heated air duct for greater than a preselected interval to determine an operational value of the preselected criterion.

15. A method as recited in claim 14, wherein the alarm signal is generated if the operational value of the preselected criterion is greater than approximately 5 ppm/minute.

16. A method as recited in claim 9, wherein the preselected criterion is measured in the immediate area outside of the heated air duct in the improper space.

17. A method for detecting improper venting of a combustion appliance within an interior space, comprising the steps of:
   providing a combustion appliance;
   operating the appliance in a manner to generate products of combustion, including carbon dioxide;
   providing an interior space into which venting of the products of combustion is improper;
   directing the products of combustion away from the interior space;
   providing a carbon dioxide detector within the interior space;

operating the carbon dioxide detector in a manner to determine whether either of the following preselected criteria indicative of improper venting within the interior space is exceeded:
   determining whether a threshold level of carbon dioxide is exceeded; and
   either determining whether a threshold level of rate of rise of carbon dioxide concentration is exceeded or determining whether a threshold level of rate of rise of carbon dioxide concentration is exceeded over a preselected number of consecutive operational cycles of the combustion appliance; and
generating an alarm signal in response to detecting that any of said preselected criterion for venting within the interior space is exceeded.

18. A method as recited in claim 17, wherein the threshold level of carbon dioxide is approximately 4000 ppm, the threshold level of rate of rise of carbon dioxide concentration is approximately 25 ppm/minute while the combustion appliance is in operation and the number of consecutive operational cycles is 2 or more.

19. A method for detecting venting of a combustion appliance within an interior space, comprising the steps of:

providing a combustion appliance;

operating the appliance in a manner to generate products of combustion, including carbon dioxide, said combustion appliance heating air which is blown by a fan through a heated air duct that is disposed adjacent said combustion appliance;

directing the products of combustion to a flue away from the interior space;

providing a carbon dioxide detector within the heated air duct;

establishing a preselected criterion for carbon dioxide within the heated air duct that is indicative of venting of products of combustion into the interior space;

operating the carbon dioxide detector in the heated air duct in a manner to determine whether said preselected criterion for venting within the interior space is exceeded; and generating an alarm signal in response to detecting that said preselected criterion for venting within the interior space is exceeded.

\* \* \* \* \*